United States Patent [19]

Thran et al.

[11] 4,281,066
[45] Jul. 28, 1981

[54] TRANSPORTABLE APPARATUS FOR TAKING SAMPLES FOR MICROBIOLOGICAL, PARTICULARLY BACTERIOLOGICAL TESTS FROM SURFACES

[76] Inventors: Volker Thran, Allmandstr. 9, 7000 Stuttgart; Werner Treige, Waldenserstr. 14, 1000 Berlin, both of Fed. Rep. of Germany

[21] Appl. No.: 102,474

[22] Filed: Dec. 11, 1979

[30] Foreign Application Priority Data

Dec. 14, 1978 [DE] Fed. Rep. of Germany ....... 2853956

[51] Int. Cl.³ .......................... C12M 1/26; C12Q 1/24
[52] U.S. Cl. ........................................ 435/292; 435/30
[58] Field of Search .......................... 15/321, 322, 302; 435/30, 292, 803, 287; 239/124, 693

[56] References Cited

U.S. PATENT DOCUMENTS

| | | | |
|---|---|---|---|
| 3,711,891 | 1/1973 | Conway | 15/321 |
| 3,713,987 | 1/1973 | Low et al. | 435/30 X |
| 3,747,155 | 7/1973 | Koellisch | 15/321 X |
| 3,919,729 | 11/1975 | Cannan | 15/321 X |
| 4,019,218 | 4/1977 | Cyphert | 15/321 |
| 4,074,387 | 2/1978 | Arato et al. | 15/322 |
| 4,153,968 | 5/1979 | Perkins | 15/321 |
| 4,164,055 | 8/1979 | Townsend | 15/321 |

*Primary Examiner*—Robert J. Warden
*Attorney, Agent, or Firm*—Steele, Gould & Fried

[57] ABSTRACT

A transportable apparatus for microbiological investigations and examinations, particularly for determining numbers of microorganisms in surface samples taken from foodstuffs, walls, etc. using a sterile rinsing liquid atomized by a compressed gas. The apparatus, which may be shaped like a pistol is provided with a container for collecting the mixture of compressed gas, rinsing liquid and rinsed-off particles and a compressed gas supply connection is provided with a valve. The nozzle of the apparatus is placed on and pressed against the surface under investigation, after which the rinsing liquid is applied by the compressed gas to the surface under investigation and is subsequently collected in the container.

43 Claims, 7 Drawing Figures

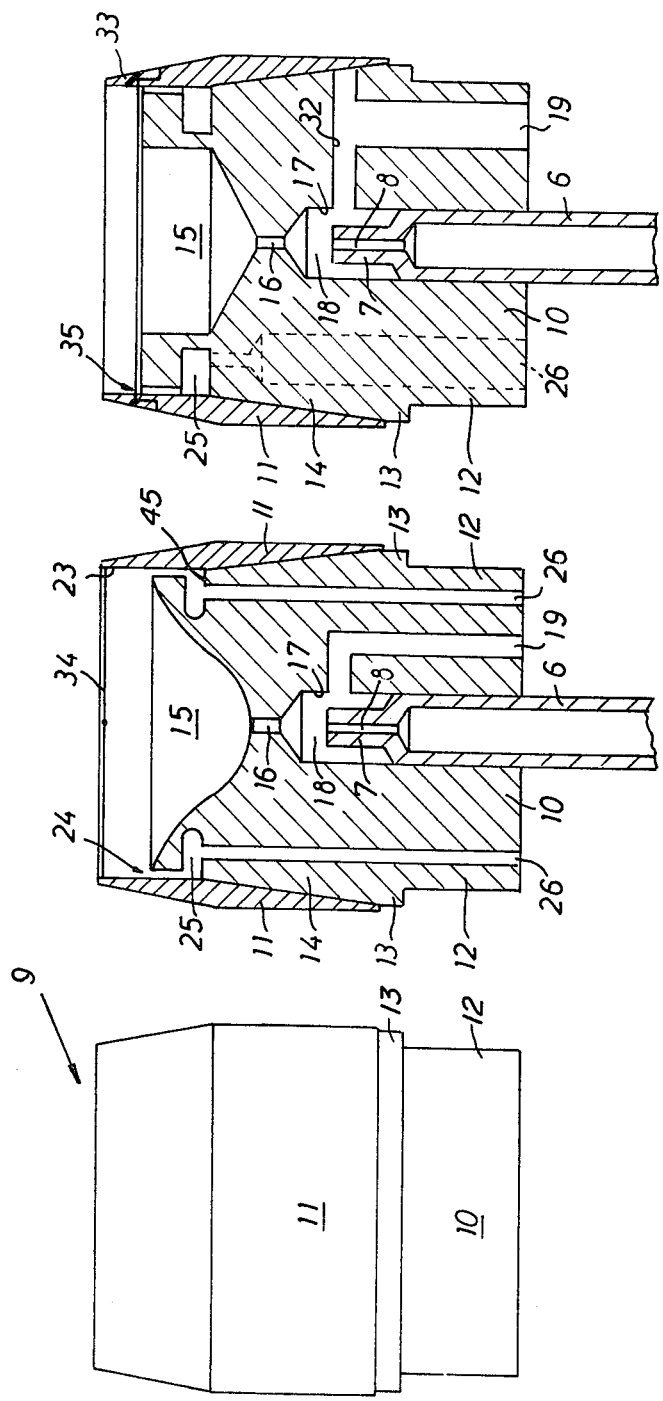

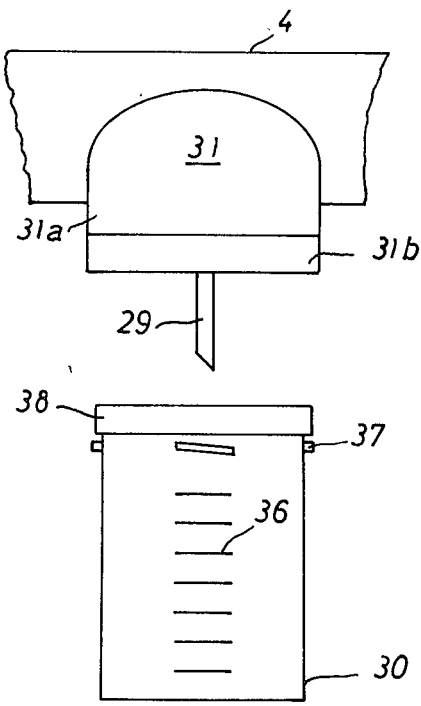
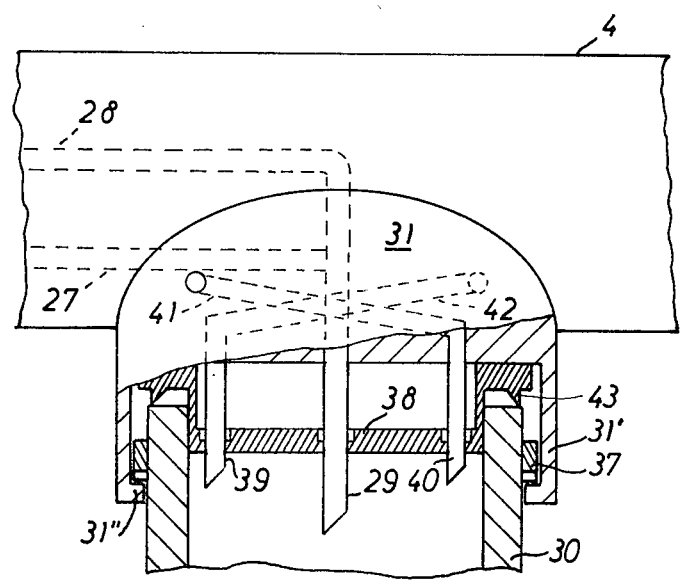
Fig. 6
Fig. 7

TRANSPORTABLE APPARATUS FOR TAKING SAMPLES FOR MICROBIOLOGICAL, PARTICULARLY BACTERIOLOGICAL TESTS FROM SURFACES

BACKGROUND OF THE INVENTION

The invention relates to a transportable apparatus for taking samples for microbiological, particularly bacteriological tests from surfaces by means of a rinsing liquid atomized by means of a compressed gas, preferably air using a compressed gas supply connection, a rinsing liquid supply connection, an atomizer and a nozzle which can be placed on the surface to be tested, into which can be introduced the compressed gas and the atomized rinsing liquid and which has a drainage line for removing the mixture of compressed gas, rinsing liquid and rinsed off particles and which is connectable by means of a collecting pipe to a collecting tank for the mixture constituted by the rinsing liquid and the rinsed off particles.

Nowadays very high demands are made regarding the hygienic aspects of the activities of manufacturers, processors and traders in foodstuffs and breeders, importers and traders in animals in order to prevent illnesses to both humans and animals, as well as the development of infectious diseases. It is up to food chemists, microbiologists and veterinary surgeons to ensure that the corresponding regulations are adhered to and the fulfilment of this task imposes that the greatest care be taken by their assistants, which is time-consuming and costly, so that it is generally only carried out on a spot check basis. To ensure that incorrect results are not obtained greatest care must be taken during sampling. This applies not only in cases where it is a question of testing materials from which samples can be taken, e.g. with foods, but also in cases where it is a question of investigating the surfaces of objects, e.g. the walls of a dairy or the skin of a chicken, where it is generally difficult to take samples. In order to obtain comparable values it would be advantageous if a standard surface, i.e. a surface area of given size could always be used as a basis. Thus, an apparatus of the above-defined type has already been developed and was described on pp 407 ff of the CANADIAN JOURNAL OF MICROBIOLOGY in 1965. However, this apparatus involves a considerable equipment expenditure and has disadvantages, which have hitherto been prejudicial to its use in practice. A main disadvantage of this apparatus it that its construction leads to a particularly unsatisfactory action, which can be attributed to the fact that only a small part of the atomized rinsing liquid can act on the surface being tested, while the remainder of the said liquid is prevented from doing so by a pressure cushion, which has built up in the nozzles just after the start of operations. This pressure cushion deflects a large part of the atomized rinsing liquid in unused form into the collecting tank, without coming into contact with the surface under investigation. Another disadvantage of this apparatus is that, due to the construction, it can only be used for sampling on vertical surfaces, i.e. cannot be universally used.

BRIEF SUMMARY OF THE INVENTION

The object of the invention is to obviate these disadvantages and provide an apparatus of the above-described type, which is much more efficient and can be used on a universal basis, i.e. independently of the position of the surface being investigated or tested.

According to the invention this object is achieved by an apparatus of the type described hereinbefore in which the drainage pipe is immediately adjacent to the free end of the nozzle and is arranged around the periphery of the nozzle in such a way that, while avoiding the formation of a pressure cushion, it is ensured that all the rinsing liquid can act on the surface being tested.

The drainage pipe of the apparatus according to the invention preferably has an annular slot issuing into the rim area of the nozzle. This slot preferably issues into an annular shoulder provided in the vicinity of the free end of the nozzle and to which is connected a frontal sealing lip pointing towards the surface being tested and particular reference will be made to this hereinafter.

The drainage pipe can also comprise a plurality of openings distributed over the periphery and issuing into the rim area of the nozzle.

The manufacture of the nozzle of the inventive apparatus and its sterilizability can be simplified in that said nozzle comprises two nestable and tightly interconnectable portions, the outer portion carrying or having the above-mentioned sealing lip.

According to a preferred embodiment of the apparatus according to the invention with the drainage line in the inner nozzle portion is associated an annular duct linked with a collecting line, which is covered by the outer nozzle portion and communicates with the inner nozzle portion. The sealing lip of the nozzle of the apparatus according to the invention is preferably constructed in an interchangeable manner so that it can be adapted to the surface under investigation. For investigating uneven surfaces the sealing lip can be elastic. For investigating flexible surfaces, e.g. the skin of an animal the nozzle of the present apparatus can have at its free end at least one support portion over the nozzle opening. This support portion can be a web or a grating, the latter preferably comprising two crosswise-arranged thin wires.

To facilitate sterilisation the components of the apparatus according to the invention are preferably made from heat-resistant materials.

Manipulation of the apparatus according to the invention can be improved by a tightly sealable and preferably transparent container having air holes being associated with and communicating with the rinsing liquid supply connection and/or its collecting line.

The container or containers preferably have a scale which is visible from the outside and can be closed by a cover having inlets and/or outlets. The container and the container cover can be screwed together, but according to a preferred embodiment they are interconnectable by a bayonet joint.

The apparatus according to the invention has in an embodiment, which is preferred due to its easy manipulation, the shape of a pistol, whose grip carries the compressed gas supply connection and whose mouth carries the nozzle, while the atomizer is arranged within its barrel. The handling of this embodiment of the apparatus can be further improved by firmly connecting at least one of the two container covers with the barrel and preferably at least one of the two container covers it rotatable with the barrel about an axis which is perpendicular thereto and this will be described in detail hereinafter.

To prevent outside infections at least one of the two containers has an intermediate cover which tightly seals it, which is preferably detachably connected therewith and only gives access to the container just before the start of operations. This intermediate cover preferably is made from a perforatable material. To facilitate working with a thus constructed container the supply and discharge lines can be constructed with ends for perforating the intermediate cover.

The compressed gas supply line preferably contains a gas filter, which is preferably interchangeable, while in the embodiment of the invention in which the apparatus is shaped like a pistol it is preferably arranged in the grip thereof.

To prevent outside infections and/or damage to the nozzle, the latter preferably has a cover or cap.

The compressed gas supply can be regulated by means of a manually operable valve, optionally arranged in the pistol grip. A pressure switch is preferable provided in the pistol grip for operating this valve.

The nozzle is preferably constructed in interchangeable manner in the present apparatus for adapting to the surface being investigated or for changing the size of the surface under investigation.

The construction of the apparatus according to the invention can be considerably simplified by arranging the atomizer in the rear end of the nozzle, as is the case in a preferred embodiment of which more details will be given hereinafter.

The nozzle of the inventive apparatus preferably has a central, axial bore used for supplying the mixture of compressed gas and atomized rinsing liquid. If the atomizer is arranged in the rear end of the nozzle, the latter preferably comprises a substantially cylindrical chamber provided in the rear area of the nozzle, into whose front area laterally issues a feed line for the rinsing liquid to be atomized. A cylindrical insert, whose external diameter preferably corresponds to the internal diameter of the cylindrical chamber is insertable into the latter. The front end of the insert is tapered and has a central bore, preferably constructed as a stepped bore, so that in the area of the tapering insert end its diameter is smaller than in the remainder of the insert, which gives the advantage that said insert can easily be replaced and can therefore be separately cleaned and, if necessary, replaced by another insert with different internal dimensions if this appears desirable for obtaining other atomization conditions.

BRIEF DESCRIPTION OF THE DRAWINGS

The invention is described in greater detail hereinafter relative to preferred, non-limitative embodiments and with reference to the drawings, wherein:

FIG. 3 is a side view of a nozzle of an apparatus according to the invention.

FIGS. 4 and 5 are in each case an axial section through a nozzle of an apparatus according to the invention with an insert.

FIG. 6 is a collecting container for the apparatus according to the invention.

FIG. 7 is a part sectional view of a collecting container and the cover associated therewith.

DETAILED DESCRIPTION OF THE PREFERRED EMBODIMENTS

Figure 1:
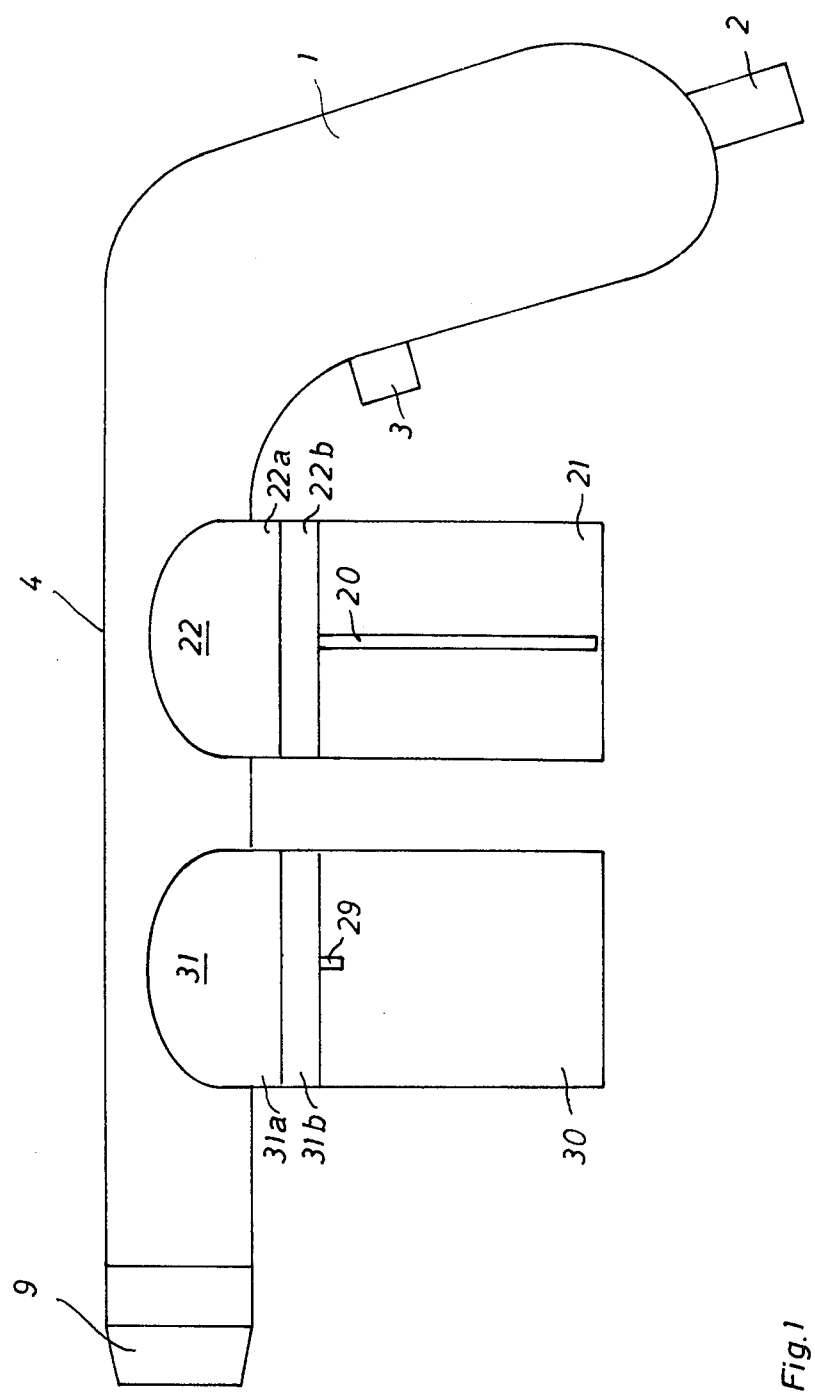
FIG. 1 is a side view of an apparatus according to the invention.
Figure 2:
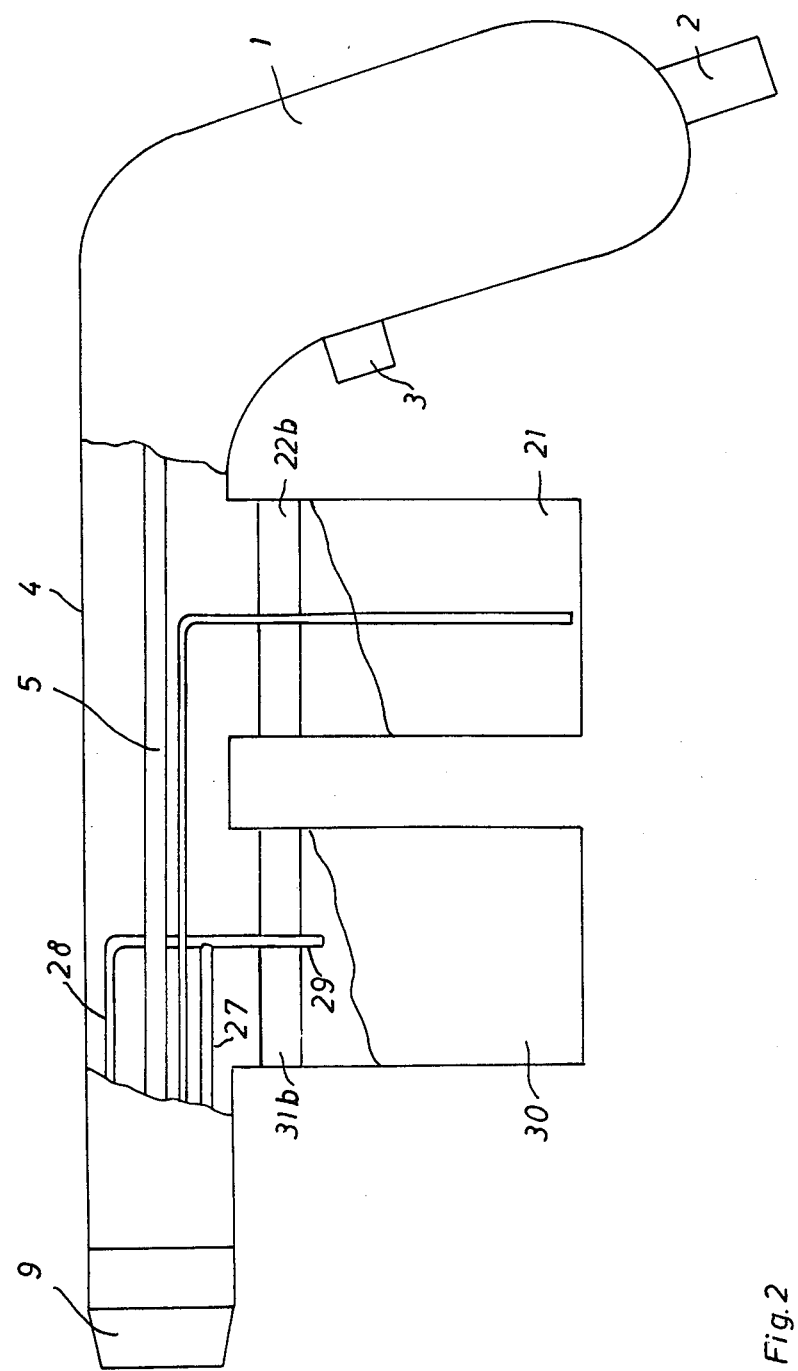
FIG. 2 is the apparatus of FIG. 1, partly in section.

The apparatus shown in FIGS. 1 and 2 is shaped like a pistol, the compressed gas supply connection 2 for the apparatus being located on the grip 1 thereof. The compressed gas supply is regulatable by means of a valve, not shown in the drawing, operable by a spring-loaded pressure switch 3 arranged in the pistol grip 1. For the further conveyance of the compressed gas supply to the pistol the pistol barrel 4 contains an axially directed line 5, whose free end is connected to an insert 6. Insert 6 is substantially cylindrical and is tapered at its front end 7, having a central bore 8, in the form of a stepped bore, whose diameter is smaller in the vicinity of the tapered insert end 7 than in the remainder of the insert. The free upwardly directed end of said insert 6 (FIGS. 4 and 5) forms part of an atomizer, located in the rear area of a nozzle 9 inserted in the mouth of the pistol barrel 4.

Nozzle 9 comprises two nestable and tightly interconnectable portions, an inner portion 10 and an outer portion 11. The inner nozzle portion 10 has a rear, cylindrical section 12 and a following, substantially frustum-shaped, front section 14 connectable to section 12 by means of a shoulder 13. Front section 14 contains a central, forwardly widening recess 15, which can be trough-shaped (cf FIG. 4) or funnel-shaped (cf FIG. 5). Recess 15 is connected by means of a central slender bore 16 with a following central bore 17, whose internal diameter corresponds to the external diameter of insert 6. Insert 6 is inserted into bore 17 to such an extent that the end of its tapered front end 7 is spaced from the transition of bore 16 with bore 17. The space surrounding the tapered insert end 7 forms an atomizing chamber 18 to which can be laterally supplied rinsing liquid by means of a bore 19 provided in the inner nozzle portion 10, a line 20 tightly interconnected with bore 19 leading to the latter. Line 20 ends close to the bottom of a substantially cylindrical, glass rinsing liquid container 21, whose cover 22 is fixed to the pistol barrel 4.

If compressed gas flows through line 5 and the connected insert 6 through atomizing chamber 18 and the linked slender bore 16, this leads to a vacuum in bore 19, which in turn leads to the sucking in of rinsing liquid through line 20. As soon as it enters atomizing chamber 18 the rinsing liquid is atomized by the compressed gas flowing through this chamber and together with the latter passes through bore 16 into the open via the recess 15 provided on the free end of inner nozzle portion 10.

The outer nozzle portion 11 is substantially annular and has in its rear lower area (FIGS. 3 to 5) a frustum-shaped recess whose conicity corresponds to the frustum-shaped section 14 of the inner nozzle portion 10. This frustum-shaped recess is followed by a cylindrical recess 23, whose diameter is greater than the front external diameter of the frustum-shaped section 14 of the inner nozzle 10, so that in the area of the cylindrical recess 23 and in the inner nozzle portion 10 there is an annular slot 24 issuing into the rim area of nozzle 9. The free, upwardly directed end of the outer nozzle portion 11 (FIGS. 3 to 5) forms a thin, annular sealing lip with which the nozzle 9 can be placed on the surface to be investigated. Slot 24 formed by an annular shoulder 45, communicates with a duct or annular slot 25 in the front area of inner nozzle portion 10 and bounded on one side by the inner wall of outer nozzle portion 11. Bore 26 emanating from the rear end of the inner nozzle portion 10 issue into duct 25. Lines 27 and 28, which in turn pass into a line 29 are connected to the bores 26. The free end of line 29 projects into a substantially cylindrical, glass collecting container 30, whose cover 31 is fixed to the pistol barrel 4.

By means of the above-described apparatus it is possible to take samples for microbiological, particularly bacteriological investigations or examinations from surfaces in the following manner:

Firstly the complete apparatus is sterilised. A predetermined quantity of sterile rinsing liquid is then introduced into the sterilised rinsing liquid container 21, which is then tightly connected with its cover 22 fixed to the pistol barrel 4. Subsequently or simultaneously collecting container 30 is connected to its cover 31 which is also fixed to the pistol barrel 4. A line leading to a compressor or a compressed gas cylinder is then connected to the compressed gas supply connection 2. When these preparations are at an end sampling can commence. The apparatus is placed on the surface under investigation by its nozzle 9. On actuating the pressure switch 3 compressed gas flows through it so that, as stated hereinbefore, rinsing liquid is sucked out of the rinsing liquid container 21 and atomized in the atomizing chamber 18. The mixture of compressed gas and atomized rinsing liquid passes through the slender bore 16 into the trough or funnel-shaped recess 15 at the free end of the inner nozzle portion 10 and strikes against the surface under investigation. Particles (microorganisms, dust particles, etc.) are hereby rinsed off the said surface. The mixture of compressed gas, atomized rinsing liquid and rinsed off particles is forced radially outwards by the after-flowing mixture of compressed gas and atomized rinsing liquid and passes through slot 24 and duct 25 via bores 26 and the following lines 27, 28 and 29 to the collecting container 30, whose cover 31 has air holes, not shown, through which the consumed compressed gas can escape. The cover 22 of rinsing liquid container 21 has air holes, not shown, to prevent a vacuum from forming, with the resulting suction problems. Sampling is at an end as soon as the rinsing liquid container 21 is completely empty. Collecting container 30 can then be unscrewed and its content can be microbiologically examined in the conventional manner. As microbiological examinations are not generally carried out at the sampling point a separate transporting cover, not shown in the drawings, is provided for the container 30.

If desired, the outer nozzle portion 11 can be replaced by another outer nozzle portion 11 having a sealing lip with a different configuration, in order to ensure that the surface characteristics of the surface under investigation can be taken into account and so that in each case surfaces with approximately the same area can be investigated. If rough surfaces, e.g. plastered walls are to be tested it is recommended that an external nozzle portion with an elastic sealing lip is used, while when investigating soft surfaces, e.g. the skin of a chicken an outer nozzle portion should be used which has on its free end a support portion passing over the nozzle mouth and which can comprise a thin wire or a wire grating, thereby preventing a bulge and consequently an increase in the size of the surface under investigation.

The line 20 projecting into the rinsing liquid container 21 is preferably constructed in such a way that its free end, following gravity, always points towards the bottom of the container or, when the pistol is inclined, towards the lower container corner, for which purpose the line is preferably elastic and has a weight at its free end.

In the case of the nozzle embodiment of FIG. 4 two diametrically facing bores 26 are provided, which serve to remove the mixture of compressed gas, atomized liquid and rinsed off particles, while at a limited radial distance between them is located the bore 19 for supplying the rinsing liquid to the atomizing chamber 18. Bore 19 passes into a radially directed recess leading into the atomizing chamber 18, said recess being relatively difficult to manufacture. In the nozzle embodiment of FIG. 5 the bores 26 for removing the mixture of compressed gas, atomized liquid and rinsed off particles are not diametrically facing, but are instead arranged on one side of the nozzle, while on the other side thereof is provided the bore 19 for supplying the rinsing liquid, said bore passing into the radially directed bore 32. On one side bore 32 leads to atomizing chamber 18 and is sealed on the other side.

To ensure that liquid does not escape from the air holes, not shown, in container covers 22 and 31 when the pistol is inclined said covers can comprise two rotatably interconnected parts, an upper cover part 22a, 31a fixed to the pistol barrel 4 and a lower cover part 22b, 31b connected in rotatable manner with the upper part and having an air hole and with which container 21, 30 can be connected, preferably by means of a bayonet joint which operates on the push, twist and lock principle.

An interchangeable sealing lip 33 (of FIG. 5) and/or nozzle 9 can be provided at its free end with a support means 34 (cf FIG. 4) to permit adaptation to the characteristics of the surface under investigation.

The support means 34 preferably comprises a grating formed by two thin wires which cross one another. The interchangeable sealing lip 33 need not be made from the same material as the supporting outer nozzle portion 11. The interchangeable sealing lip is preferably made from an elastic material, e.g. rubber.

The slot 24 can be replaced by a plurality of openings 35 distributed over the periphery and issuing into the rim area of nozzle 9 (cf FIG. 5).

The compressed gas necessary for atomizing the rinsing liquid can be supplied to the apparatus according to the invention from a portable small compressor or from an also portable compressed gas cylinder, so that there is no need for a long compressed gas line, thus increasing the number of possible uses and improving the manipulation of the apparatus according to the invention.

The collecting container 30 and/or the liquid container 21 is preferably in the form of a transparent glass beaker, having a lateral scale 36. Dogs 37, forming part of a bayonet joint are shaped onto the upper edge area of said beaker and by means of these the beaker is connectable with its cover 31 or its lower part 31b. To prevent outside infections the unused beaker 30 preferably has an intermediate cover 38, which is preferably stuck thereto and which tightly seals the same. This intermediate cover 38 is preferably made from a material which can be perforated by means of a cannula, e.g. a thin plastic foil. In the embodiment of FIG. 6 the intermediate cover 38 is constructed in dish-shaped manner and its edge engages laterally on the beaker wall. However, the intermediate cover 38 can also be disc-like and engage on the beaker edge. The lower part 31b of the container cover 31 is provided the above-mentioned line 29 for supplying the mixture of compressed gas, atomized rinsing liquid and rinsed off particles. The free end of line 29 is constructed in cannula-like manner, so that it is in a position to pass through the intermediate cover 38 when container 31 is connected to its cover.

A cover 31 fixed to the barrel 4 is associated with the collecting container 30 of FIG. 7. Cover 31 has a substantially cylindrical edge 31', whose free end has inwardly directed projections 31", forming a bayonet joint with the dogs 37 on container 30, said joint permitting the connection of the container and its cover. In the upper, solidly constructed region of cover 30 is centrally guided line 29 which serves to supply the mixture of compressed gas, atomized rinsing liquid and rinsed off particles. In this embodiment line 29 is also cannula-like at its free end. In the upper area of cover 31 there are also two diametrically facing tubes 39, 40, whose free ends are also cannula-like. Tubes 39, 40 are connected to the outside air by means of lines 41, 42 arranged in cross-like manner in the upper cover area, so that container 30 can be vented by means of tubes 39, 40.

Collecting container 30 shown in FIG. 7 has an intermediate cover 38, which essentially comprises a thin plate having an edge engaging on the inner wall of the container and whose free end is bent outwards and has a sealing lip 43 pointing towards the edge of the container. In FIG. 7 cover 38 has thinner portions, which are dimensioned and arranged in such a way that they can easily be perforated by the cannula-like ends of line 29 and tubes 39, 40 as soon as beaker 30 is pressed against its cover 31. In the embodiment of FIG. 7 cover 38 is constructed and dimensioned in such a way that it tightly seals container 30, but is not so firmly connected with the latter that it necessarily follows the rotary movement which has to be effected by the container for its bayonet-like connection with the cover. As a result this rotary movement does not produce intermediate cover cracks and consequently said intermediate cover reliably protects the container cover 31 from being infected by the microorganisms entering container 30.

The collecting container 30 of FIG. 7 can be vented in a satisfactory manner by tubes 39, 40 in cases where inclined surfaces have to be investigated, where the longitudinal axis of the container is necessarily inclined, because even when the container is in an extreme inclined position one of the two tube openings is located above the container liquid level.

The intermediate cover 38 can be made from elastic material, preferably heat-resistant rubber and has sealable openings for the supply/discharge lines and the venting lines, said openings in each case preferably having at least one inwardly directed sealing edge ensuring a complete seal of the line.

In the represented embodiments the supply line and discharge line are in each case arranged in such a way that their longitudinal axis continuously coincides with the associated container. However, it is also possible for the free ends of said lines to run eccentrically in the vicinity of the container wall, providing an articulated connection between the initially centrally located line area and the eccentrically located line area.

A back-flow prevention device is preferably provided in the supply line and/or discharge line. This device can preferably comprise, for example, a vented siphon or a ball valve. A back-flow can also be prevented by back-suction.

If the free end of the discharge line is not centrally arranged, but is instead located in the vicinity of the container wall, the base of the latter preferably has a central, e.g. conical projection, which ensures that the container content can be virtually completely sucked out by means of the discharge line.

The invention is not limited to the embodiments described and represented hereinbefore and various modifications can be made thereto without passing beyond the scope of the invention.

What is claimed is:

1. A transportable apparatus for taking microbiological and bacteriological test samples from surfaces by use of a rinsing liquid atomized by a compressed gas, comprising:
   a compressed gas supply connection;
   a rinsing liquid supply connection;
   a nozzle, having a free end which can be placed on and pressably engage the surface;
   an atomizer disposed in the nozzle, through which the compressed gas flows from the compressed gas supply connection, drawing the rinsing liquid through the rinsing liquid supply connection, the atomized rinsing liquid being sprayed onto the surface;
   a discharge line immediately adjacent the free end of the nozzle and arranged around the periphery thereof, for removing a mixture of compressed gas, rinsing liquid and rinsed-off particles formed under the nozzle; and,
   a collecting tank connection in fluid communication with the discharge line through which the mixture is urged only by pressure from after flowing compressed gas in the nozzle, thereby obviating the need for a vacuum source downstream from the nozzle.

2. An apparatus according to claim 1, wherein a free end of the nozzle is defined by a rim and the discharge line comprises an annular slot issuing into the nozzle adjacent the rim.

3. An apparatus according to claim 2, wherein the slot issues into an annular shoulder provided in the vicinity of the free end of the nozzle and further comprising a frontal sealing lip directed towards the surface under investigation.

4. An apparatus according to claim 3, wherein the sealing lip is removably attached.

5. An apparatus according to claim 3, wherein the sealing lip is elastic.

6. An apparatus according to claim 2, wherein the discharge line comprises a plurality of openings distributed around the periphery of the nozzle and issuing into the nozzle adjacent the rim.

7. An apparatus according to claim 1, wherein the discharge line comprises a plurality of openings distributed over the periphery of the nozzle and issuing into the nozzle adjacent the rim.

8. An apparatus according to claim 1, wherein the nozzle comprises two nestable and tightly interconnectable portions, the outer portion carrying a sealing lip for engaging the surface.

9. An apparatus according to claim 8, wherein the nozzle is detachably mounted.

10. An apparatus according to claim 8, wherein the discharge line comprises a slot and a duct, formed in the inner nozzle portion, communicating with the collecting tank connection and circumferentially bounded by the outer nozzle portion.

11. An apparatus according to claim 10, wherein the sealing lip is elastic.

12. An apparatus according to claim 10, wherein the individual components thereof are in each case made from heat-resistant, sterilizable materials.

13. An apparatus according to claim 1, wherein the nozzle has support means passing over the free end of the nozzle for engaging the surface.

14. An apparatus according to claim 13, wherein the support means is a grating.

15. An apparatus according to claim 14, wherein the grating comprises two thin criss-crossed wires.

16. An apparatus according to claim 1, wherein the individual components thereof are in each case made from heat-resistant, sterilizable material.

17. An apparatus according to claim 1, further comprising tightly sealable, transparent containers connected to the rinsing liquid supply connection and the collecting tank connection.

18. An apparatus according to claim 17, wherein each of the supply and discharge connections comprises a line leading into the associated container, each line having a portion which enters the container centrally and an eccentrically directed portion within the container, respective portions being joined by an articulated connection.

19. An apparatus according to claim 17, wherein each of the containers comprises a cover provided with discharge openings and air inlet/outlet openings.

20. An apparatus according to claim 19, wherein each of the containers is detachably and threadably connected to its cover.

21. An apparatus according to claim 19, wherein each of the containers is detachably connected with its cover by a rapid-action bayonet coupling.

22. An apparatus according to claim 19, essentially shaped like a pistol, having a grip, barrel and barrel mouth, the grip bearing the compressed gas supply connection, the mouth carrying the nozzle, and the atomizer being disposed in the barrel.

23. An apparatus according to claim 22, wherein at least one of the two container covers is fixed to the barrel.

24. An apparatus according to claim 22, wherein at least one of the two container covers is rotatable with respect to the barrel about an axis which is perpendicular to the latter.

25. An apparatus according to claim 22, wherein at least one of the two containers has an intermediate cover which tightly seals the container.

26. An apparatus according to claim 25, wherein the intermediate cover comprises sealable openings.

27. An apparatus according to claim 26, wherein the openings have in each case at least one inwardly directed sealing edge.

28. An apparatus according to claim 25, wherein at least one of the two containers is detachably connected with its associated intermediate cover.

29. An apparatus according to claim 28, wherein the intermediate cover is made from a perforatable material.

30. An apparatus according to claim 29, wherein the supply connectors comprise respective supply and discharge lines so constructed as to be able to perforate the intermediate cover.

31. An apparatus according to claim 1, essentially shaped like a pistol, having a grip, barrel and barrel mouth, the grip bearing the compressed gas supply connection, the mouth carrying the nozzle, and the atomizer being disposed in the barrel.

32. An apparatus according to claim 31, further comprising a manually operable valve for regulating the compressed gas supply, disposed in the pistol grip, the valve having a pressure switch for operating the valve.

33. An apparatus according to claim 31, wherein the mouth of the barrel has a central bore through which a mixture formed from the compressed gas and the atomized rinsing liquid enters the free end of the nozzle.

34. An apparatus according to claim 1, further comprising a gas filter in the compressed gas supply line.

35. An apparatus according to claim 1, further comprising a cap for the nozzle.

36. An apparatus according to claim 1, further comprising a manually operable valve for regulating the compressed gas supply.

37. An apparatus according to claim 1, wherein the nozzle is detachably mounted.

38. An apparatus according to claim 1, wherein the atomizer is located at the end of the nozzle opposite the free end.

39. An apparatus according to claim 1, wherein the nozzle has a central bore through which a mixture formed from the compressed gas and the atomized rinsing liquid enters the free end of the nozzle.

40. An apparatus according to claim 1, wherein the atomizer comprises a substantially cylindrical chamber located in the part of the nozzle opposite the free end and a feed line communicating with the rinsing liquid supply connection, the feed line having a front part issuing laterally into the chamber.

41. An apparatus according to claim 40, further comprising a tapered cylindrical insert whose largest external diameter corresponds to the internal diameter of the cylindrical chamber and which has a tapered front end and a tapered central bore.

42. An apparatus according to claim 41, wherein the tapered central bore of the tapered cylindrical insert is a stepped bore, the stepped bore being smallest at the front end of the insert.

43. An apparatus according to claim 1, wherein each of the supply and discharge lines is provided with means for preventing a reverse fluid flow.

* * * * *